United States Patent
Komaki

(10) Patent No.: US 10,210,876 B2
(45) Date of Patent: Feb. 19, 2019

(54) AUDIO DEVICE AND COMPUTER-READABLE PROGRAM

(71) Applicant: D&M Holdings, Inc., Kanagawa (JP)

(72) Inventor: Masato Komaki, Kanagawa (JP)

(73) Assignee: D&M Holdings, Inc., Kanagawa (JP)

(*) Notice: Subject to any disclaimer, the term of this patent is extended or adjusted under 35 U.S.C. 154(b) by 0 days.

(21) Appl. No.: 15/522,403

(22) PCT Filed: Sep. 7, 2015

(86) PCT No.: PCT/JP2015/075331
§ 371 (c)(1),
(2) Date: Apr. 27, 2017

(87) PCT Pub. No.: WO2016/067753
PCT Pub. Date: May 6, 2016

(65) Prior Publication Data
US 2017/0330571 A1  Nov. 16, 2017

(30) Foreign Application Priority Data
Oct. 30, 2014  (JP) .................. 2014-221417

(51) Int. Cl.
*G10L 19/02* (2013.01)
*H04L 29/08* (2006.01)
(Continued)

(52) U.S. Cl.
CPC .............. *G10L 19/02* (2013.01); *G10L 21/00* (2013.01); *H04L 67/306* (2013.01); *H04R 5/04* (2013.01);
(Continued)

(58) Field of Classification Search
None
See application file for complete search history.

(56) References Cited

U.S. PATENT DOCUMENTS 6,192,341 B1* 2/2001 Becker ................ G06F 3/04897
345/471
7,564,979 B2* 7/2009 Swartz .................. A61B 5/121
381/312
(Continued)

FOREIGN PATENT DOCUMENTS

JP  11-109985  4/1999
JP  2000-209698  7/2000
(Continued)

*Primary Examiner* — Douglas Godbold
(74) *Attorney, Agent, or Firm* — Peter A. Nieves; Sheehan Phinney Bass & Green PA

(57) ABSTRACT

[Problem] To provide an audio device with which it is possible to efficiently utilize the storage capacity of a storage device for storing audio data. [Solution] In this audio device 1, in accordance with user profile information stored in a profile information storage unit 102, audio data inputted to an audio data input unit 103 is subjected by a filter unit 104 to a process of cutting a frequency band higher than the highest frequency audible to the user) and/or a frequency band lower than the lowest frequency audible to the user, and the data is then encoded by a codec unit 105, and stored to an audio storage device 100. Audio data can thereby be stored in the audio storage device 100 in compressed form with no noticeable decline in sound quality to the user, making it possible to store more audio data, such as music, in the audio storage device 100.

8 Claims, 4 Drawing Sheets

(51) Int. Cl.
*G10L 21/00* (2013.01)
*H04R 5/04* (2006.01)
*A61B 5/12* (2006.01)
*H04R 25/00* (2006.01)
*G11B 20/10* (2006.01)

(52) U.S. Cl.
CPC ..... *A61B 5/121* (2013.01); *G11B 2020/10564* (2013.01); *H04R 25/70* (2013.01); *H04R 2205/041* (2013.01)

(56) References Cited

U.S. PATENT DOCUMENTS

| | | | |
|---|---|---|---|
| 2002/0068986 A1* | 6/2002 | Mouline | A61B 5/121 700/94 |
| 2003/0028385 A1* | 2/2003 | Christodoulou | H04R 5/04 704/278 |
| 2006/0235688 A1* | 10/2006 | Bicego | G10L 13/04 704/254 |
| 2014/0288685 A1* | 9/2014 | Haefeli | H04R 25/75 700/94 |
| 2015/0194154 A1* | 7/2015 | Lee | H04N 5/60 704/246 |
| 2015/0326965 A1* | 11/2015 | Sprague | G10L 13/043 381/317 |

FOREIGN PATENT DOCUMENTS

| | | |
|---|---|---|
| JP | 2001-283521 | 10/2001 |
| JP | 2001-308100 | 11/2001 |
| JP | 2002-540480 | 11/2002 |
| JP | 2004-135220 | 4/2004 |
| JP | 2008-209846 | 8/2006 |
| JP | 2009-210826 | 9/2009 |

* cited by examiner

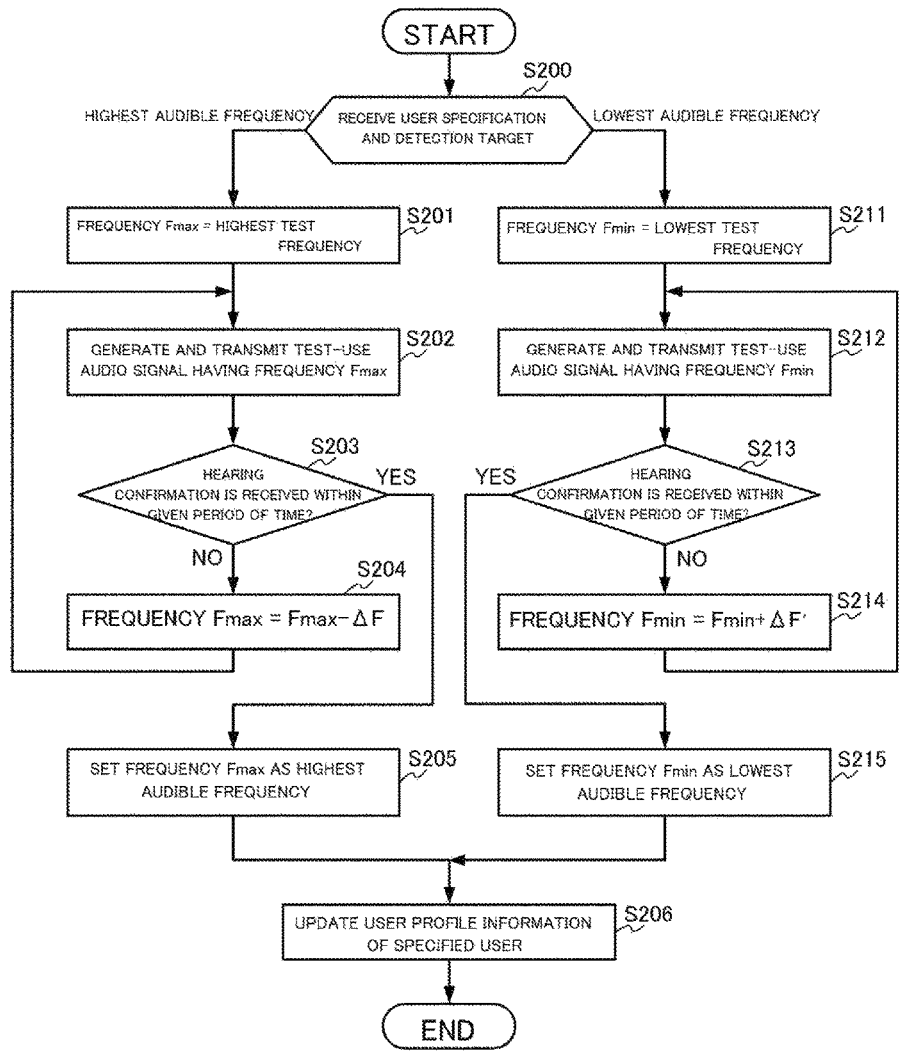

AUDIO DEVICE AND COMPUTER-READABLE PROGRAM

CROSS-REFERENCE TO RELATED APPLICATIONS

This application is the National Stage of International Application No. PCT/JP2015/075331, filed Sep. 7, 2015, which claims the benefit of Japanese Patent Application No. 2014-221417, filed Oct. 30, 2014. The contents of these prior applications are incorporated by reference herein in their entirety.

TECHNICAL FIELD

The present invention relates to an audio device configured to store audio data in a storage device, or an audio device configured to transmit audio data stored in a storage device over a network.

BACKGROUND ART

Hitherto, there has been known a type of audio device configured to encode audio data output from a CD player or the like to store the encoded data on a memory card or a similar storage device, or decode audio data stored on a storage device to play the decoded data from a speaker (see, for example, Patent Literature 1).

CITATION LIST

Patent Literature

[PTL 1] JP 2001-283521 A

SUMMARY OF INVENTION

Technical Problem

In general, data in an audible frequency band between 20 Hz and 20 kHz is used as audio data of CD-DA or the like.

A frequency band that is actually audible, however, varies from person to person. For instance, young people tend to have difficulty in hearing sounds in a low frequency band while elderly people tend to have difficulty in hearing sounds in a high frequency band. Audio devices of the related art do not consider such differences in actual audible frequency band among individuals, and handle the audible frequency band between 20 Hz and 20 kHz uniformly. This results in a failure to make full use of the storage capacity of a memory card or a similar storage device in which audio data is stored. This also leads to ineffective use of the communication band of a wireless LAN or a similar network in the case where played audio is transmitted over the network to a network speaker, a portable terminal, or other transmission destinations.

The present invention has been made in view of the circumstances described above, and an object of the present invention is therefore to provide an audio device capable of making full use of the storage capacity of a storage device in which audio data is stored. Another object of the present invention is to provide an audio device capable of effectively using the communication band of a network over which audio data is transmitted.

Solution to Problem

In order to attain the objects described above, according to one aspect of the present invention, audio data to be stored is compressed by cutting, from the data to be stored, at least one of a frequency band higher than the highest audible frequency of a user and a frequency band lower than the lowest audible frequency of the user. The compressed audio data to be stored is then stored on a memory card or a similar storage device.

For example, according to one aspect of the present invention, there is provided an audio device, which is configured to store audio data in a storage device, including:
  profile information storage means for storing user profile information, which includes at least one of a highest audible frequency of a user and a lowest audible frequency of the user;
  audio input means for receiving input of audio data to be stored;
  frequency band cutting means for cutting, when audio data is input to the audio input means and user profile information stored in the profile information storage means includes the highest audible frequency, a frequency band higher than the highest audible frequency from the input audio data, and cutting, when audio data is input to the audio input means and user profile information stored in the profile information storage means includes the lowest audible frequency, a frequency band lower than the lowest audible frequency from the input audio data; and
  audio storage control means for storing, in the storage device, the audio data from which a frequency band has been cut by the frequency band cutting means.

Further, according to another aspect of the present invention, audio data to be transmitted is compressed by cutting, from the data to be transmitted, at least one of a frequency band higher than the highest audible frequency of a user and a frequency band lower than the lowest audible frequency of the user. The compressed audio data to be transmitted is then transmitted over a network to a network speaker, a portable terminal, or other transmission destinations.

For example, according to another aspect of the present invention, there is provided an audio device, which is configured to transmit audio data over a network, including:
  profile information storage means for storing, for each user, user profile information, which includes at least one of a highest audible frequency of the each user and a lowest audible frequency of the each user;
  frequency band cutting means for cutting, when the audio data is transmitted and a piece of the user profile information that is stored in the profile information storage means in association with a user who is a transmission destination of the audio data includes the highest audible frequency, a frequency band higher than the highest audible frequency from the audio data, and cutting, when the audio data is transmitted and a piece of the user profile information that is stored in the profile information storage means in association with a user who is the transmission destination of the audio data includes the lowest audible frequency, a frequency band lower than the lowest audible frequency from the audio data; and
  audio transmission means for transmitting the audio data from which a frequency band has been cut by the frequency band cutting means to the transmission destination of the audio data over the network.

Advantageous Effects of Invention

According to the present invention, audio data is stored in a storage device, or is transmitted to a transmission destination over a network, after at least one of a frequency band higher than the highest audible frequency of a user and a frequency band lower than the lowest audible frequency of the user is cut from the audio data. The audio data can therefore be stored in the storage device in a compressed state without allowing a drop in sound quality to be felt by the user. This enables the audio device to store a larger amount of audio data, for example, more tunes, in the storage device, thereby making full use of the storage capacity of the storage device in which audio data is stored. In addition, audio data can be transmitted over a network to a transmission destination in a compressed state without allowing a drop in sound quality to be felt by the user. The chance of the audio data transmission overwhelming the communication band of the network is therefore reduced, and the communication band of the network over which audio data is transmitted can be used effectively.

BRIEF DESCRIPTION OF DRAWINGS

FIG. 4 is a flow chart for illustrating an audible range detection test of the audio device 2.

DESCRIPTION OF EMBODIMENTS

Referring to the accompanying drawings, embodiments of the present invention are described below.

First Embodiment

Figure 1:
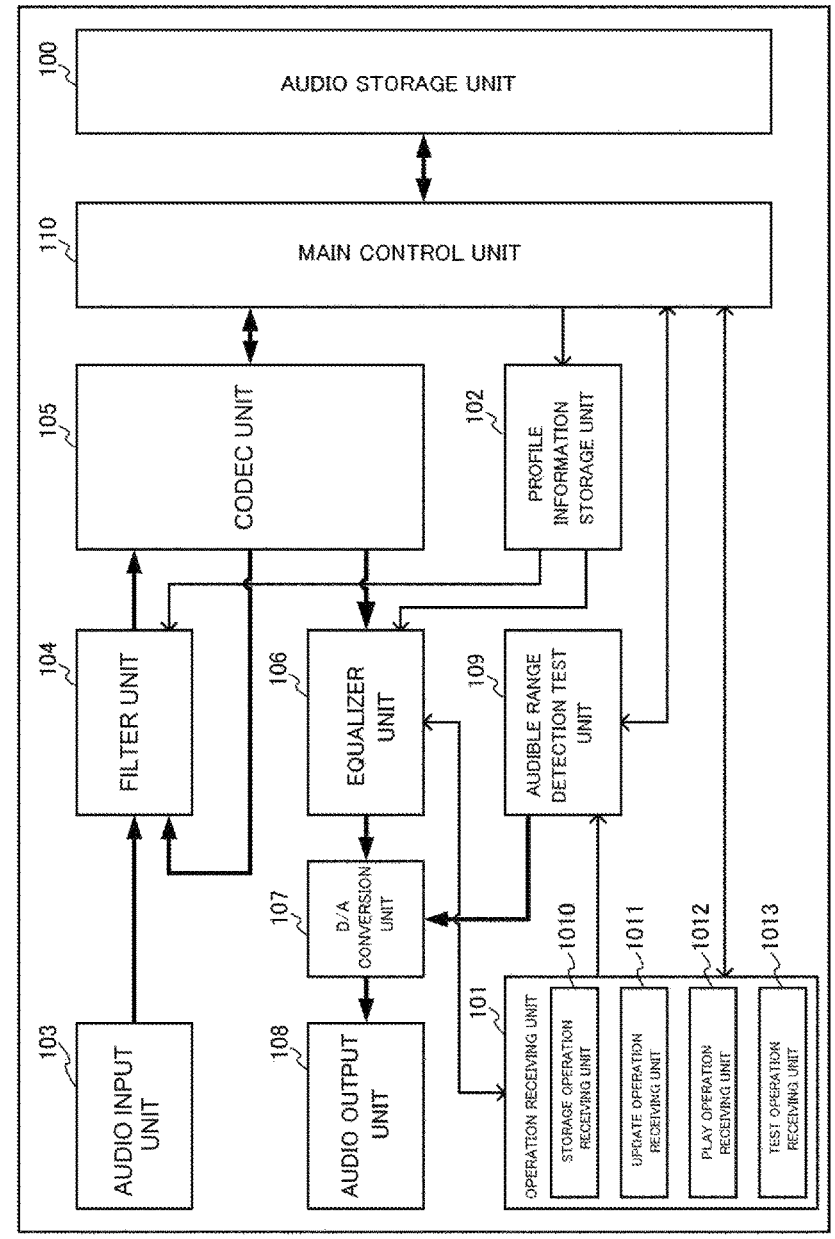
FIG. 1 is a schematic function block diagram of an audio device 1 according to a first embodiment of the present invention.

FIG. 1 is a schematic function block diagram of an audio device 1 according to a first embodiment of the present invention.

The audio device 1 according to the first embodiment includes, as illustrated in FIG. 1, an audio storage unit 100, an operation receiving unit 101, a profile information storage unit 102, an audio input unit 103, a filter unit 104, a codec unit 105, an equalizer unit 106, a D/A conversion unit 107, an audio output unit 108, an audible range detection test unit 109, and a main control unit 110.

The audio storage unit 100 is configured to store audio data encoded by the codec unit 105.

The operation receiving unit 101 is configured to receive various types of operation from a user. As illustrated in FIG. 1, the operation receiving unit 101 includes a storage operation receiving unit 1010 configured to receive the operation of storing audio data in the audio storage unit 100, an update operation receiving unit 1011 configured to receive the operation of updating audio data that is stored in the audio storage unit 100, a play operation receiving unit 1012 configured to receive the operation of playing audio data that is stored in the audio storage unit 100, and a test operation receiving unit 1013 configured to receive operation of an audible range detection test, which is described later.

The profile information storage unit 102 is configured to store user profile information, which includes at least one of the highest audible frequency of the user and the lowest audible frequency of the user.

The audio input unit 103 is an interface through which CD-DA or other types of audio data are input from a CD player or a similar device to the audio device 1.

The filter unit 104 is configured to filter audio data to be processed that has been input to the audio input unit 103 or that has been decoded by the codec unit 105, based on the user profile information stored in the profile information storage unit 102, thereby cutting a desired frequency band from this audio data.

The codec unit 105 is configured to encode audio data processed by the filter unit 104. The codec unit 105 is also configured to decode already encoded audio data read out of the audio storage unit 100.

The equalizer unit 106 is configured to adjust the level of audio data decoded by the codec unit 105, for each frequency band obtained by dividing, into a given number of frequency bands (the given number is determined by resolution), the frequency band of an input range that is set as indicated by the user profile information stored in the profile information storage unit 102.

The D/A conversion unit 107 is configured to convert audio data whose level has been adjusted by the equalizer unit 106 into an analog audio signal.

The audio output unit 108 is configured to output an analog audio signal converted from audio data by the D/A conversion unit 107 to a speaker, headphones, or the like.

The audible range detection test unit 109 is configured to conduct an audible range detection test, which is described later, in order to detect at least one of the highest audible frequency of the user and the lowest audible frequency of the user.

The main control unit 110 is configured to control the units 100 to 109 of the audio device 1 in an integrated manner.

The operation of the thus configured audio device 1 is described next.

The description given first is about the operation of audio data storing processing. This operation is started when the main control unit 110 receives storage operation from the user via the storage operation receiving unit 1010 of the operation receiving unit 101.

When audio data is input to the audio input unit 103, the filter unit 104 filters the input audio data based on the user profile information stored in the profile information storage unit 102. Specifically, in the case where the user profile information includes the highest audible frequency of the user, a frequency band higher than the highest audible frequency is cut from the audio data input to the audio input unit 103. In the case where the user profile information includes the lowest audible frequency of the user, a frequency band lower than the lowest audible frequency is cut from the audio data input to the audio input unit 103. The filter unit 104 outputs the filtered audio data to the codec unit 105. The codec unit 105 encodes the audio data received from the filter unit 104, and outputs the encoded audio data to the main control unit 110. In response to this, the main control unit 110 stores the encoded audio data received from the codec unit 105 in the audio storage unit 100.

The operation of audio data updating processing is described next. This operation is started when the main control unit 110 receives, from the user via the update operation receiving unit 1011 of the operation receiving unit 101, update operation along with the specification of encoded audio data that is stored in the audio storage unit 100.

The main control unit 110 reads the encoded audio data specified by the update operation out of the audio storage unit 100, and passes the read data to the codec unit 105. The codec unit 105 decodes the encoded audio data received from the main control unit 110, and passes the decoded data to the filter unit 104. The filter unit 104 receives the decoded audio data from the codec unit 105, and filters this audio data based on the user profile information stored in the profile information storage unit 102. Specifically, in the case where the user profile information includes the highest audible frequency of the user, a frequency band higher than the highest audible frequency is cut from the audio data decoded by the codec unit 105. In the case where the user profile information includes the lowest audible frequency of the user, a frequency band lower than the lowest audible frequency is cut from the audio data decoded by the codec unit 105. The filter unit 104 outputs the filtered audio data to the codec unit 105. The codec unit 105 re-encodes the audio data received from the filter unit 104, and outputs the re-encoded audio data to the main control unit 110. In response to this, the main control unit 110 rewrites the encoded audio data that is specified by the update operation and that is found among audio data stored in the audio storage unit 100 with the re-encoded audio data received from the codec unit 105.

In the first embodiment, the user specifies one piece of audio data at a time as data to be updated with audio data from which a frequency band has been cut. In the case where the specification of a plurality of pieces of audio data is received from the user, the specified pieces of audio data may sequentially be updated with audio data from which a frequency band has been cut. For instance, in the case where the specification of an audio data folder and the specification of an update time are received, processing of updating all pieces of audio data that are stored in the specified folder with audio data from which a frequency band has been cut may be started when the update time arrives.

The operation of audio data play processing is described next. This operation is started when the main control unit 110 receives, from the user via the play operation receiving unit 1012 of the operation receiving unit 101, play operation along with the specification of encoded audio data that is stored in the audio storage unit 100.

The main control unit 110 reads the encoded audio data specified by the play operation out of the audio storage unit 100, and passes the read data to the codec unit 105. The codec unit 105 decodes the encoded audio data received from the main control unit 110, and passes the decoded data to the equalizer unit 106. The equalizer unit 106 receives the decoded audio data from the codec unit 105, and adjusts the level of this audio data for each frequency band that is obtained by dividing, into a given number of frequency bands (the given number is determined by resolution), the frequency band of an input range that is set as indicated by the user profile information stored in the profile information storage unit 102. Specifically, in the case where the user profile information includes the highest audible frequency of the user, the equalizer unit 106 sets this highest audible frequency as the maximum value of the input range. A given first reference frequency (for example, 20 kHz) is set as the maximum value of the input range in the case where the user profile information does not include the highest audible frequency. In the case where the user profile information includes the lowest audible frequency of the user, the equalizer unit 106 sets this lowest audible frequency as the minimum value of the input range. A given second reference frequency (for example, 20 Hz), which is lower than the first reference frequency, is set as the minimum value of the input range in the case where the user profile information does not include the lowest audible frequency. The input range identified by the maximum frequency value and the minimum frequency value that are set in this manner is divided into the given number of frequency bands and, for each frequency band obtained by the division, the level of audio data is adjusted by following preset information or an instruction that is received from the user via the play operation receiving unit 1012. The equalizer unit 106 outputs the audio data adjusted in level to the D/A conversion unit 107. The D/A conversion unit 107 converts the audio data input from the equalizer unit 106 into an analog audio signal, and the analog audio signal is output from the audio output unit 108.

Figure 2:
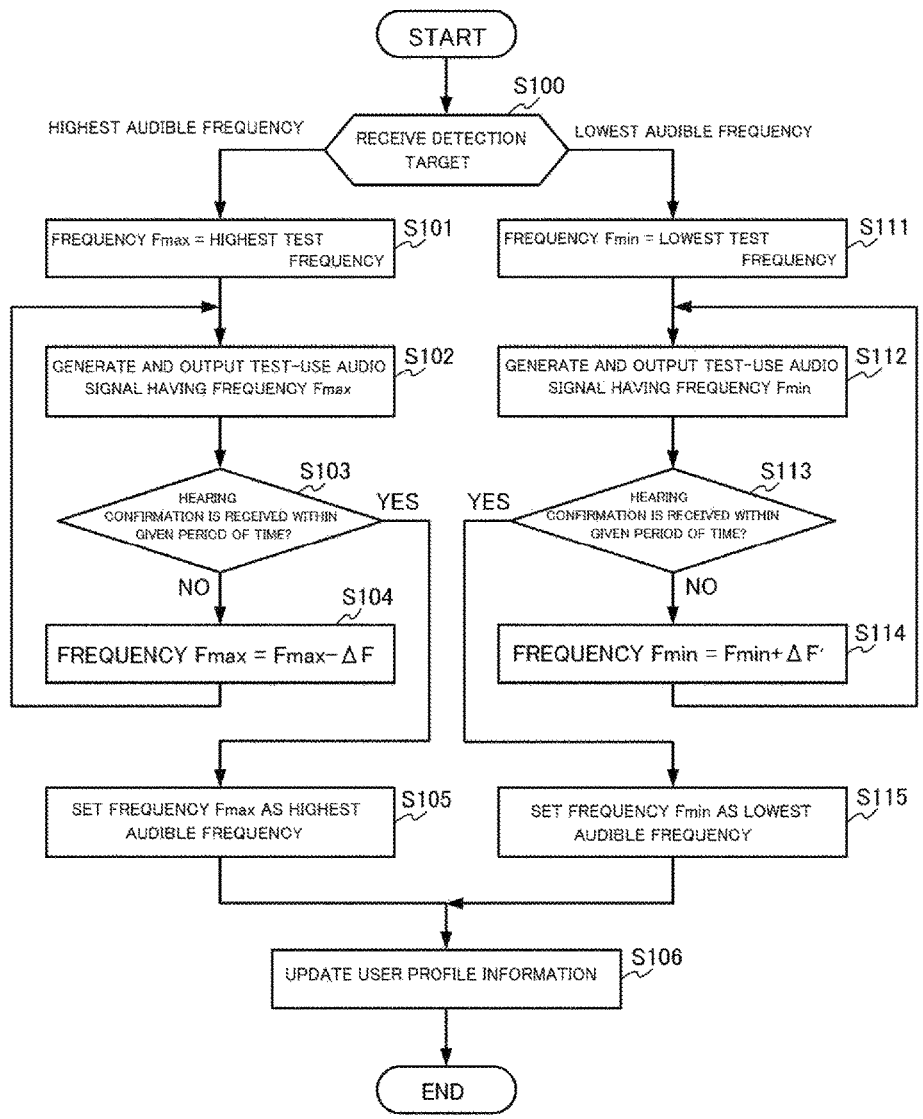
FIG. 2 is a flow chart for illustrating an audible range detection test of the audio device 1.

The audible range detection test of the audio device 1 is described next. FIG. 2 is a flow chart for illustrating the audible range detection test of the audio device 1. This flow is started when the main control 110 receives audible range detection test starting operation from the user via the test operation receiving unit 1013 of the operation receiving unit 101.

First, the test operation receiving unit 1013 receives from the user specification regarding which of the user's highest audible frequency and the user's lowest audible frequency is to be detected, and notifies the details of the specification to the main control unit 110 (Step S100). The main control unit 110 instructs the audible range detection test unit 109 to detect the highest audible frequency when the detection of the highest audible frequency is specified by the user via the test operation receiving unit 1013 ("highest audible frequency" in Step S100), and then proceeds to Step S101. When the detection of the lowest audible frequency is specified by the user via the test operation receiving unit 1013 ("lowest audible frequency" in Step S100), on the other hand, the main control unit 110 instructs the audible range detection test unit 109 to detect the lowest audible frequency, and then proceeds to Step S111.

In Step S101, the audible range detection test unit 109 sets a frequency parameter Fmax to the highest test frequency (for example, the maximum value of an audible frequency band that is employed in CD-DA or similar audio data (e.g., 20 kHz)) that is determined in advance. The audible range detection test unit 109 next generates test-use audio data that has the frequency set to the frequency parameter Fmax, and outputs the generated data to the D/A conversion unit 107. The D/A conversion unit 107 converts the test-use audio data input from the audible range detection test unit 109 into an analog audio signal (test-use audio signal), and the audio signal is output from the audio output unit 108 (Step S102).

Thereafter, the audible range detection test unit 109 waits for the user to perform, via the test operation receiving unit 1013, hearing confirmation operation, which indicates that the test-use audio signal is successfully heard by the user. When the hearing confirmation operation is not performed within a given period of time (for example, 10 seconds) ("NO" in Step S103), the audible range detection test unit 109 newly sets the frequency parameter Fmax to a frequency that is lower than the current set value of the frequency parameter Fmax by a given frequency ΔF (for example, 1 kHz) (Step S104). The audible range detection test unit 109 then returns to Step S102. When the hearing confirmation operation is performed within the given period of time ("YES" in Step S103), on the other hand, the current set value of the frequency parameter Fmax is set as the highest audible frequency of the user (Step S105). This highest audible frequency is notified to the main control unit 110.

In response to this, the main control unit 110 stores user profile information that includes the notified highest audible frequency in the profile information storage unit 102. When user profile information is already stored and the existing user profile information includes no highest audible frequency, the notified highest audible frequency is added to the existing user profile information (Step S106). When the existing user profile information includes the highest audible frequency, the highest audible frequency included in the existing user profile information is updated with the newly set highest audible frequency (Step S106).

In Step S111, the audible range detection test unit 109 sets a frequency parameter Fmin to the lowest test frequency (for example, the minimum value of an audible frequency band that is employed in CD-DA or similar audio data (e.g., 20 Hz)) that is determined in advance to be lower than the highest test frequency. The audible range detection test unit 109 next generates test-use audio data that has the frequency set to the frequency parameter Fmin, and outputs the generated data to the D/A conversion unit 107. The D/A conversion unit 107 converts the test-use audio data input from the audible range detection test unit 109 into an analog audio signal (test-use audio signal), and the audio signal is output from the audio output unit 108 (Step S112).

Thereafter, the audible range detection test unit 109 waits for the user to perform, via the test operation receiving unit 1013, hearing confirmation operation, which indicates that the test-use audio signal is successfully heard by the user. When the hearing confirmation operation is not performed within a given period of time (for example, 10 seconds) ("NO" in Step S113), the audible range detection test unit 109 newly sets the frequency parameter Fmin to a frequency that is higher than the current set value of the frequency parameter Fmin by a given frequency ΔF' (for example, 1 Hz) (Step S114). The audible range detection test unit 109 then returns to Step S112. When the hearing confirmation operation is performed within the given period of time ("YES" in Step S113), on the other hand, the current set value of the frequency parameter Fmin is set as the lowest audible frequency of the user (Step S115). This lowest audible frequency is notified to the main control unit 110.

In response to this, the main control unit 110 stores user profile information that includes the notified lowest audible frequency in the profile information storage unit 102. When user profile information is already stored and the existing user profile information includes no lowest audible frequency, the notified lowest audible frequency is added to the existing user profile information (Step S106). When the existing user profile information includes the lowest audible frequency, the lowest audible frequency included in the existing user profile information is updated with the newly set lowest audible frequency (Step S106).

This concludes the description on the first embodiment of the present invention.

In the first embodiment, the filter unit 104 cuts at least one of a frequency band higher than the highest audible frequency of the user and a frequency band lower than the lowest audible frequency of the user from audio data input to the audio input unit 103, and the filtered audio data is stored in the audio storage unit 100. The audio data can therefore be stored in the audio storage unit 100 in a compressed state without allowing a drop in sound quality to be felt by the user. This enables the audio device 1 to store audio data of more tunes in the audio storage unit 100, thereby making full use of the storage capacity of the audio storage unit 100.

In the first embodiment, the filter unit 104 cuts a frequency band higher than the highest audible frequency of the user and a frequency band lower than the lowest audible frequency of the user from audio data read out of the audio storage unit 100, and the audio data is then written back to the audio storage unit 100. Audio data stored in the audio storage unit 100 is thus updated with further compressed audio data, which enables the audio device 1 to make even fuller use of the storage capacity of the audio storage unit 100.

In the first embodiment, the audible range detection test unit 109 outputs a test-use audio signal while decreasing the frequency gradually from a level that is determined as the highest test frequency (for example, the maximum value of an audible frequency band), and asks the user to confirm whether the test-use audio signal is successfully heard by the user, to thereby detect the highest audible frequency of the user. The audible range detection test unit 109 also outputs a test-use audio signal while increasing the frequency gradually from a level that is determined as the lowest test frequency (for example, the minimum value of the audible frequency band), and asks the user to confirm whether the test-use audio signal is successfully heard by the user, to thereby detect the lowest audible frequency of the user. The highest audible frequency and lowest audible frequency of the user can therefore be detected with precision to be registered in the user profile information.

In the first embodiment, the equalizer unit 106 adjusts the level of audio data to be played for each frequency band obtained by dividing, into a given number of frequency bands, the frequency band of an input range that is set based on two frequencies (the highest audible frequency and lowest audible frequency of the user) included in the user profile information. This prevents the allocation of a frequency band with which the user has difficulty in hearing to the frequency band of the input range, and a finer level adjustment can be made within a frequency band in which the user can actually hear sounds.

In the first embodiment, the audio storage unit 100 can be a memory card or a similar removable storage medium. The audio storage unit 100 may also be a network-attached storage (NAS) or a similar storage that is connected via a network.

In the first embodiment, the audible range detection test unit 109 outputs a test-use audio signal while gradually decreasing the frequency in order to detect the highest audible frequency of the user, but may instead detect the highest audible frequency of the user by outputting a test-use audio signal while gradually increasing the frequency and asking the user to confirm whether the test-audio signal is successfully heard by the user. The audible range detection test unit 109 may also detect the lowest audible frequency of the user by outputting a test-use audio signal while gradually decreasing the frequency and asking the user to confirm whether the test-use audio signal is successfully heard by the user.

In the first embodiment, the function configuration of the audio device 1 that is illustrated in FIG. 1 may be implemented by hardware with the use of an application-specific integrated circuit (ASIC), a field programmable gate array (FPGA), or other integrated logic circuits, or may be implemented by software with the use of a digital signal processor (DSP), a microcomputer, or other computers. Alternatively, the function configuration of FIG. 1 may be implemented on a PC, a PDA, a smartphone, or other computer systems that include a CPU, a memory, and an auxiliary storage device, for example, an HDD or a DVD-ROM, by the CPU by loading a given program onto the memory from the auxiliary storage device.

Second Embodiment

Figure 3:
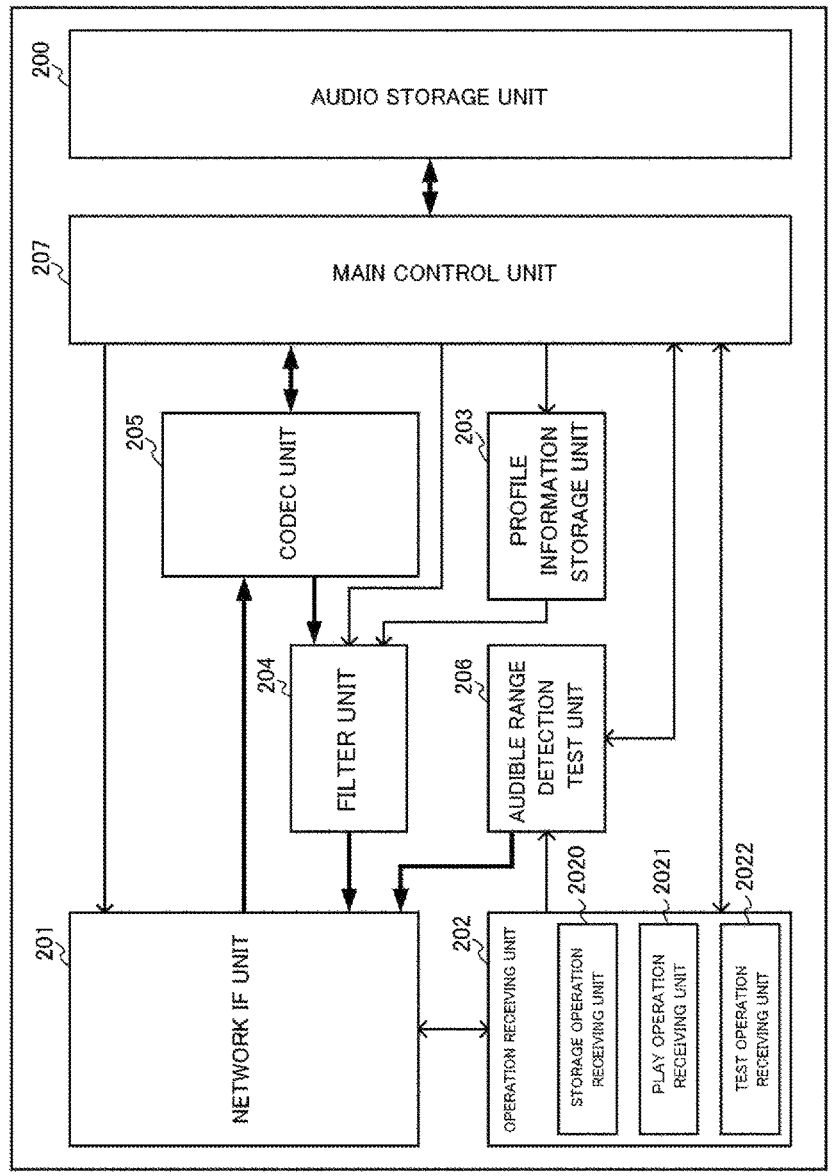
FIG. 3 is a schematic function block diagram of an audio device 2 according to a second embodiment of the present invention.

FIG. 3 is a schematic function block diagram of an audio device 2 according to a second embodiment of the present invention.

The audio device 2 according to the second embodiment includes, as illustrated in FIG. 3, an audio storage unit 200, a network IF unit 201, an operation receiving unit 202, a profile information storage unit 203, a codec unit 205, a filter unit 204, an audible range detection test unit 206, and a main control unit 207.

The audio storage unit 200 is configured to store audio data encoded by the codec unit 205.

The network IF unit 201 is an interface configured to hold communication over a wireless LAN or other networks to and from a network speaker, a PC, a portable terminal, or other network terminals that have an audio playing function.

The operation receiving unit 202 is configured to receive various types of operation from a user of a network terminal via the network IF unit 201. As illustrated in FIG. 3, the operation receiving unit 202 includes a storage operation receiving unit 2020 configured to receive the operation of storing audio data in the audio storage unit 200, a play operation receiving unit 2021 configured to receive the operation of playing audio data that is stored in the audio storage unit 200, and a test operation receiving unit 2022 configured to receive operation of an audible range detection test, which is described later.

The profile information storage unit 203 is configured to store, for each user of a network terminal, user profile information, which includes at least one of the highest audible frequency of the user and the lowest audible frequency of the user.

The codec unit 205 is configured to encode audio data received from a network terminal via the network IF unit 201. The codec unit 205 is also configured to decode already encoded audio data read out of the audio storage unit 200.

The filter unit 204 is configured to filter audio data to be processed that has been decoded by the codec unit 205, based on the user profile information stored in the profile information storage unit 203 in association with the user notified by the main control unit 207, thereby cutting a desired frequency band from this audio data.

The audible range detection test unit 206 is configured to conduct an audible range detection test, which is described later, in order to detect at least one of the highest audible frequency of the user and the lowest audible frequency of the user.

The main control unit 207 is configured to control the units 200 to 206 of the audio device 2 in an integrated manner.

The operation of the thus configured audio device 2 is described next.

The description given first is about the operation of audio data storing processing. This operation is started when the storage operation receiving unit 2020 of the operation receiving unit 202 receives storage operation from a network terminal via the network IF unit 201, and notifies the reception of the storage operation to the main control unit 207.

First, the main control unit 207 transmits, to the network terminal on which the storage operation has been performed, via the network IF unit 201, a request to transmit audio data to be stored. Next, the codec unit 205 receives the audio data from the network terminal via the network IF unit 201, encodes this audio data, and outputs the encoded audio data to the main control unit 207. In response to this, the main control unit 207 stores the encoded audio data received from the codec unit 205 in the audio storage unit 200.

The operation of audio data playing processing is described next. This operation is started when the play operation receiving unit 2021 of the operation receiving unit 202 receives, from a network terminal via the network IF unit 201, play operation along with the specification of a user of the network terminal and the specification of encoded audio data stored in the audio storage unit 200, and notifies the reception of the play operation to the main control unit 207.

First, the main control unit 207 reads the encoded audio data specified by the play operation out of the audio storage unit 200, and passes the read data to the codec unit 205. The main control unit 207 also notifies the user specified by the play operation to the filter unit 204, and notifies the network terminal on which the play operation has been performed to the network IF unit 201. The codec unit 205 decodes the encoded audio data received from the main control unit 207, and passes the decoded data to the filter unit 204. The filter unit 204 receives the decoded audio data from the codec unit 205, and filters this audio data based on the user profile information stored in the profile information storage unit 203 in association with the user notified by the main control unit 207. Specifically, in the case where the user profile information includes the highest audible frequency of the user, a frequency band higher than the highest audible frequency is cut from the audio data decoded by the codec unit 205. In the case where the user profile information includes the lowest audible frequency of the user, a frequency band lower than the lowest audible frequency is cut from the audio data decoded by the codec unit 205. The filter unit 204 outputs the filtered audio data to the network IF unit 201. The network IF unit 201 receives the audio data from the filter unit 204, and transmits this audio data to the network terminal notified by the main control unit 207.

The audible range detection test of the audio device 2 is described next. FIG. 4 is a flow chart for illustrating the audible range detection test of the audio device 2. This flow is started when the test operation receiving unit 2022 of the operation receiving unit 202 receives audible range detection test starting operation from a network terminal via the network IF unit 201, and notifies the reception of the audible range detection test starting operation to the main control unit 207.

First, the test operation receiving unit 2022 receives, from the network terminal via the network IF unit 201, along with specification of a user, specification regarding which of the user's highest audible frequency and the user's lowest audible frequency is to be detected, and notifies the details of the specification to the main control unit 207 (Step S200). The main control unit 207 instructs the audible range detection test unit 206 to detect the highest audible frequency when the detection of the highest audible frequency is notified by the test operation receiving unit 2022 ("highest audible frequency" in Step S200), and then proceeds to Step S201. When the detection of the lowest audible frequency is notified by the test operation receiving unit 2022 ("lowest audible frequency" in Step S200), on the other hand, the main control unit 207 instructs the audible range detection test unit 206 to detect the lowest audible frequency, and then proceeds to Step S211.

In Step S201, the audible range detection test unit 206 sets a frequency parameter Fmax to the highest test frequency (for example, the maximum value of an audible frequency band that is employed in CD-DA or similar audio data (e.g., 20 kHz)) that is determined in advance. The audible range detection test unit 206 next generates test-use audio data that has the frequency set to the frequency parameter Fmax, and outputs the generated data to the network IF unit 201. The network IF unit 201 transmits the test-use audio data input from the audible range detection test unit 206 to the network terminal on which the audible range detection test starting operation has been performed (Step S202).

Thereafter, the audible range detection test unit 206 waits for the reception of a hearing confirmation, which indicates that the test-use audio signal is successfully heard, from the network terminal via the test operation receiving unit 2022 and the network IF unit 201. When the hearing confirmation is not received within a given period of time (for example, 10 seconds) ("NO" in Step S203), the audible range detection test unit 206 newly sets the frequency parameter Fmax to a frequency that is lower than the current set value of the frequency parameter Fmax by a given frequency ΔF (for example, 1 kHz) (Step S204). The audible range detection test unit 206 then returns to S202. When the hearing confirmation is received within the given period of time ("YES" in Step S203), on the other hand, the current set value of the frequency parameter Fmax is set as the highest audible frequency of the user (Step S205). This highest audible frequency is notified to the main control unit 207.

In response to this, the main control unit 207 stores user profile information that includes the notified highest audible frequency in the profile information storage unit 203 in association with the specified user. When user profile information associated with the specified user is already stored and the existing user profile information includes no highest audible frequency, the notified highest audible frequency is added to the existing user profile information (Step S206). When the existing user profile information includes the highest audible frequency, the highest audible frequency included in the existing user profile information is updated with the newly set highest audible frequency (Step S206).

In Step S211, the audible range detection test unit 206 sets a frequency parameter Fmin to the lowest test frequency (for example, the minimum value of an audible frequency band that is employed in CD-DA or similar audio data (e.g., 20 Hz)) that is determined in advance to be lower than the highest test frequency. The audible range detection test unit 206 next generates test-use audio data that has the frequency set to the frequency parameter Fmin, and outputs the generated data to the network IF unit 201. The network IF unit 201 transmits the test-use audio data input from the audible range detection test unit 206 to the network terminal on which the audible range detection test starting operation has been performed (Step S212).

Thereafter, the audible range detection test unit 206 waits for the reception of a hearing confirmation, which indicates that the test-use audio signal is successfully heard, from the network terminal via the test operation receiving unit 2022 and the network IF unit 201. When the hearing confirmation is not received within a given period of time (for example, 10 seconds) ("NO" in Step S213), the audible range detection test unit 206 newly sets the frequency parameter Fmin to a frequency that is higher than the current set value of the frequency parameter Fmin by a given frequency ΔF' (for example, 1 Hz) (Step S214). The audible range detection test unit 206 then returns to Step S212. When the hearing confirmation is received within the given period of time ("YES" in Step S213), on the other hand, the current set value of the frequency parameter Fmin is set as the lowest audible frequency of the user (Step S215). This lowest audible frequency is notified to the main control unit 207.

In response to this, the main control unit 207 stores user profile information that includes the notified lowest audible frequency in the profile information storage unit 203 in association with the specified user. When user profile information associated with the specified user is already stored and the existing user profile information includes no lowest audible frequency, the notified lowest audible frequency is added to the existing user profile information (Step S206). When the existing user profile information includes the lowest audible frequency, the lowest audible frequency included in the existing user profile information is updated with the newly set lowest audible frequency (Step S206).

This concludes the description on the second embodiment of the present invention.

In the second embodiment, the filter unit 204 cuts, from audio data read out of the audio storage unit 200 under an instruction from a network terminal, at least one of a frequency band higher than the highest audible frequency of a user of this network terminal and a frequency band lower than the lowest audible frequency of the user, and the filtered audio data is transmitted to this network terminal. The audio data can therefore be transmitted via the network to the network terminal of the user in a compressed state without allowing a drop in sound quality to be felt by the user. The chance of the audio data transmission overwhelming the communication band of the network is therefore reduced, and the communication band of a network over which audio data is transmitted can be used effectively.

In the second embodiment, the audible range detection test unit 206 transmits, to a network terminal, a test-use audio signal while decreasing the frequency gradually from a level that is determined as the highest test frequency (for example, the maximum value of an audible frequency band), and receives a hearing confirmation about the test-use audio signal from the network terminal, to thereby detect the highest audible frequency of a user of this network terminal. The audible range detection test unit 206 also transmits, to a network terminal, a test-use audio signal while increasing the frequency gradually from a level that is determined as the lowest test frequency (for example, the minimum value of the audible frequency band), and receives a hearing confirmation about the test-use audio signal from the network terminal, to thereby detect the lowest audible frequency of the user of the network terminal. For each user of a network terminal, the highest audible frequency and lowest audible frequency of the user can therefore be detected with precision to be registered in the user profile information.

In the second embodiment, the audio storage unit 200 can be a memory card or a similar removable storage medium. The audio storage unit 100 may also be a network-attached storage (NAS) or a similar storage that is connected via a network.

In the second embodiment, the audible range detection test unit 206 transmits a test-use audio signal while gradually decreasing the frequency in order to detect the highest audible frequency of a user, but may instead detect the highest audible frequency of a user of a network terminal by transmitting a test-use audio signal to the network terminal while gradually increasing the frequency and receiving a hearing confirmation about the test-audio signal from the network terminal. The audible range detection test unit 206 may also detect the lowest audible frequency of a user of a network terminal by transmitting a test-use audio signal to the network terminal while gradually decreasing the frequency and receiving a hearing confirmation about the test-use audio signal from the network terminal.

In the second embodiment, the function configuration of the audio device 2 that is illustrated in FIG. 3 may be implemented by hardware with the use of an application-specific integrated circuit (ASIC), a field programmable gate array (FPGA), or other integrated logic circuits, or may be implemented by software with the use of a digital signal processor (DSP), a microcomputer, or other computers. Alternatively, the function configuration of FIG. 3 may be implemented on a PC, a PDA, a smartphone, or other computer systems that include a CPU, a memory, and an auxiliary storage device, for example, an HDD or a DVD-ROM, by the CPU by loading a given program onto the memory from the auxiliary storage device.

REFERENCE SIGNS LIST 1, 2: audio device, 100, 200: audio storage unit, 101, 202: operation receiving unit, 102, 203: profile information storage unit, 103: audio input unit, 104, 204: filter unit, 105, 205: codec unit, 106: equalizer unit, 107: D/A conversion unit, 108: audio output unit, 109, 206: audible range detection test unit, 110, 207: main control unit, 201: network IF unit, 1010, 2020: storage operation receiving unit, 1011: update operation receiving unit, 1012, 2021: play operation receiving unit, 1013, 2022: test operation receiving unit

The invention claimed is:

1. An audio device, which is configured to store audio data in an audio storage device, comprising:
  a profile information storage means for storing a user profile information, which comprises at least one of a highest audible frequency of a user and a lowest audible frequency of the user;
  an audible range detection test device, configured to conduct an audible range detection test, to detect the at least one of the highest audible frequency of the user and the lowest audible frequency of the user;
  a filter device configured to filter an input audio data based on the user profile information stored in the profile information storage means;
  audio input means for receiving audio data to be stored;
  frequency band cutting means for cutting, when audio data is input to the audio input means and user profile information stored in the profile information storage means comprises the highest audible frequency, a frequency band higher than the highest audible frequency from the input audio data, and cutting, when audio data is input to the audio input means and user profile information stored in the profile information storage means comprises the lowest audible frequency, a frequency band lower than the lowest audible frequency from the input audio data;
  audio storage control means for storing, in the audio storage device, the audio data from which a frequency band has been cut by the frequency band cutting means;
  a main control device, configured to store encoded audio data received from a codec device in the audio storage device; and
  the filter device further configured to receive a decoded audio data from the codec device, and configured to filter the decoded audio data based on the user profile information stored in the profile information storage means in association with the user notified by the main control device.

2. An audio device according to claim 1, further comprising update operation receiving means for receiving update operation along with specification of a piece of audio data that is stored in the storage device,
  wherein the audio storage control means is configured to read, when the update operation receiving means receives the update operation from the user, the piece of audio data specified by the update operation out of the storage device, output the read piece of audio data to the frequency band cutting means, and update the piece of audio data that is stored in the storage device and that is specified by the update operation with the audio data from which a frequency band has been cut by the frequency band cutting means, and
  wherein the frequency band cutting means is configured to cut, when audio data is received from the audio storage control means and user profile information stored in the profile information storage means comprises the highest audible frequency, a frequency band higher than the highest audible frequency from the received audio data, and is configured to cut, when audio data is received from the audio storage control means and user profile information stored in the profile information storage means comprises the lowest audible frequency, a frequency band lower than the lowest audible frequency from the received audio data.

3. An audio device according to claim 1, further comprising:
  test operation receiving means for receiving, from the user, audible range detection test starting operation;
  audible range detection test means for detecting, when the test operation receiving means receives the audible range detection test starting operation, at least one of the highest audible frequency of the user and the lowest audible frequency of the user by outputting audio test signals that have different frequencies in descending or ascending order of frequency level, and then receiving, for each of the audio test signals, from the user, an answer regarding whether the each of the audio test signals is heard successfully or unsuccessfully; and
  profile information storage control means for storing, in the profile information storage means, user profile information comprising at least one of the highest audible frequency and the lowest audible frequency that are detected by the audible range detection test means.

4. An audio device according to claim 1, further comprising:
  level adjusting means for adjusting a level of input audio data for each frequency band that is obtained by dividing a set frequency band into a given number of frequency bands;
  audio output means for outputting the audio data adjusted in level by the level adjusting means; and
  play operation receiving means for receiving, from the user, play operation along with specification of a piece of audio data that is stored in the storage device, wherein the audio storage control means is configured to read, when the play operation receiving means receives the play operation from the user, the piece of audio data specified by the play operation out of the storage device and output the read piece of audio data to the level adjusting means, and
  wherein the level adjusting means is configured to set the highest audible frequency as a maximum value of the set frequency band when audio data is received from the audio storage control means and user profile information stored in the profile information storage means comprises the highest audible frequency, is configured to set a given first reference frequency as the maximum value of the set frequency band when audio data is received from the audio storage control means and user profile information stored in the profile information storage means comprises no highest audible frequency, is configured to set the lowest audible frequency as a minimum value of the set frequency band when audio data is received from the audio storage control means and user profile information stored in the profile information storage means comprises the lowest audible frequency, and is configured to set a given second reference frequency, which is lower than the given first reference frequency, as the minimum value of the set frequency band when audio data is received from the audio storage control means and user profile information stored in the profile information storage means comprises no lowest audible frequency.

5. An audio device, which is configured to transmit audio data over a network, comprising:
a profile information storage means for storing, for each user, a user profile information, which comprises at least one of a highest audible frequency of the each user and a lowest audible frequency of the each user;
an audible range detection test device, configured to conduct an audible range detection test, to detect the at least one of the highest audible frequency of the user and the lowest audible frequency of the user;
a filter device configured to filter an input audio data based on the user profile information stored in the profile information storage means;
frequency band cutting means for cutting, when the audio data is transmitted and a piece of the user profile information that is stored in the profile information storage means in association with a user who is a transmission destination of the audio data comprises the highest audible frequency, a frequency band higher than the highest audible frequency from the audio data, and cutting, when the audio data is transmitted and a piece of the user profile information that is stored in the profile information storage means in association with a user who is the transmission destination of the audio data comprises the lowest audible frequency, a frequency band lower than the lowest audible frequency from the audio data;
audio transmission means for transmitting the audio data from which a frequency band has been cut by the frequency band cutting means to the transmission destination of the audio data over the network;
a main control device, configured to store encoded audio data received from a codec device in the audio storage device; and
the filter device further configured to receive a decoded audio data from the codec device, and configured to filter the decoded audio data based on the user profile information stored in the profile information storage means in association with the user notified by the main control device.

6. An audio device according to claim 5, further comprising:
test operation receiving means for receiving, from a user, audible range detection test starting operation along with specification of the user;
audible range detection test means for detecting at least one of the highest audible frequency of the user and the lowest audible frequency of the user when the test operation receiving means receives the audible detection range test starting operation, by outputting audio test signals that have different frequencies in descending or ascending order of frequency level, and then receiving, for each of the audio test signals, from the user, an answer regarding whether the each of the audio test signals is heard successfully or unsuccessfully; and
profile information storage control means for storing, in the profile information storage means, user profile information comprising at least one of the highest audible frequency and the lowest audible frequency that are detected by the audible range detection test means, in association with the user specified by the audible range detection test starting operation.

7. A program readable by a computer, the program causing the computer to function as:
a profile information storage means for storing a user profile information, which comprises at least one of a highest audible frequency of a user and a lowest audible frequency of the user;
an audible range detection test device, configured to conduct an audible range detection test, to detect the at least one of the highest audible frequency of the user and the lowest audible frequency of the user;
a filter device configured to filter an input audio data based on the user profile information stored in the profile information storage means;
audio input means for receiving audio data to be stored
frequency band cutting means for cutting, when audio data is input to the audio input means and the user profile information stored in the profile information storage means comprises the highest audible frequency, a frequency band higher than the highest audible frequency from the input audio data, and cutting, when audio data is input to the audio input means and the user profile information stored in the profile information storage means comprises the lowest audible frequency, a frequency band lower than the lowest audible frequency from the input audio data;
audio storage control means for storing, in an audio storage device, the audio data from which a frequency band has been cut by the frequency band cutting means,
a main control device, configured to store encoded audio data received from a codec device in the audio storage device; and
the filter device further configured to receive a decoded audio data from the codec device, and configured to filter the decoded audio data based on the user profile information stored in the profile information storage means in association with the user notified by the main control device, wherein
the program is stored on a non-volatile memory.

8. A program readable by a computer, the program causing the computer to function as:
a profile information storage means for storing, for each user, a user profile information, which comprises at least one of a highest audible frequency of the each user and a lowest audible frequency of the each user;
an audible range detection test device, configured to conduct an audible range detection test, to detect the at least one of the highest audible frequency of the user and the lowest audible frequency of the user;
a filter device configured to filter an input audio data based on the user profile information stored in the profile information storage means;
frequency band cutting means for cutting, when audio data is transmitted and a piece of the user profile information that is stored in the profile information storage means in association with a user who is a transmission destination of the audio data comprises the highest audible frequency, a frequency band higher than the highest audible frequency from the audio data, and cutting, when audio data is transmitted and a piece of the user profile information that is stored in the profile information storage means in association with a user who is the transmission destination of the audio data comprises the lowest audible frequency, a frequency band lower than the lowest audible frequency from the audio data; and audio transmission means for transmitting the audio data from which a frequency band has been cut by the frequency band cutting means to the transmission destination of the audio data over a network, a main control device, configured to store encoded audio data received from a codec device in an audio storage device; and the filter device further configured to receive a decoded audio data from the codec device, and configured to filter the decoded audio data based on the user profile information stored in the profile information storage means in association with the user notified by the main control device, wherein the program is stored on a non-volatile memory.

* * * * *